United States Patent
Huebner et al.

(10) Patent No.: US 8,177,819 B2
(45) Date of Patent: May 15, 2012

(54) EXPANDED FIXATION OF BONES

(75) Inventors: Randall J. Huebner, Portland, OR (US); Benone Tarcau, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 144 days.

(21) Appl. No.: 12/853,144

(22) Filed: Aug. 9, 2010

(65) Prior Publication Data

US 2010/0324602 A1   Dec. 23, 2010

Related U.S. Application Data

(63) Continuation of application No. 11/112,858, filed on Apr. 22, 2005, now abandoned.

(60) Provisional application No. 60/564,853, filed on Apr. 22, 2004.

(51) Int. Cl.
*A61B 17/88* (2006.01)
(52) U.S. Cl. .......................... 606/281; 606/71
(58) Field of Classification Search .......... 606/280–299, 606/70, 71, 86 B; 623/21.11, 21.12
See application file for complete search history.

(56) References Cited

U.S. PATENT DOCUMENTS

| | | | |
|---|---|---|---|
| 820,503 A | 5/1906 | Krengel et al. |
| 869,697 A | 10/1907 | Eilhauer et al. |
| 1,105,105 A | 7/1914 | Sherman |
| 1,345,425 A | 7/1920 | Wells |
| 1,789,060 A | 1/1931 | Weisenbach |
| 1,889,239 A | 11/1932 | Crowley |
| 2,406,832 A | 9/1946 | Hardinge |
| 2,443,363 A | 6/1948 | Townsend et al. |
| 2,486,303 A | 10/1949 | Longfellow |
| 2,489,870 A | 11/1949 | Dzus |
| 2,494,229 A | 1/1950 | Collison |
| 2,500,370 A | 3/1950 | McKibbin |
| 2,526,959 A | 10/1950 | Lorenzo |
| 2,580,821 A | 1/1952 | Nicola |
| 2,583,896 A | 1/1952 | Siebrandt |
| 2,737,835 A | 3/1956 | Herz |
| 3,025,853 A | 3/1962 | Mason |

(Continued)

FOREIGN PATENT DOCUMENTS

AU       89750/91       2/1992

(Continued)

OTHER PUBLICATIONS

Abel et al., *An Axially Mobile Plate for Fracture Fixation*, Internal Fixation in Osteoporotic Bone, pp. 279-283, 2002.

(Continued)

*Primary Examiner* — Eduardo C Robert
*Assistant Examiner* — Tara Carter
(74) *Attorney, Agent, or Firm* — Kolisch Hartwell, PC

(57) ABSTRACT

System, including methods, apparatus, and kits, for expanded bone fixation with bone plates. A bone plate and an extension plate may be provided. The bone plate may be secured to a proximal portion of a humerus and overlapping the greater tuberosity of the humerus using fasteners received in openings defined by the bone plate. The extension plate may be attached to the bone plate and the humerus using (a) a fastener disposed in an aperture defined by the first end region and in threaded engagement with the bone plate and (b) a fastener received in an aperture defined by the second end region and extending into the humerus. The attached extension plate may extend from a position over the greater tuberosity to a position over the lesser tuberosity of the humerus such that the intermediate region is disposed over a biceps tendon.

11 Claims, 3 Drawing Sheets

U.S. PATENT DOCUMENTS

| | | |
|---|---|---|
| 3,072,423 A | 1/1963 | Charlton |
| 3,171,518 A | 3/1965 | Bergmann |
| 3,244,170 A | 4/1966 | McElvenny |
| 3,346,894 A | 10/1967 | Lemelson |
| 3,386,437 A | 6/1968 | Treace |
| 3,488,779 A | 1/1970 | Christensen |
| 3,489,143 A | 1/1970 | Halloran |
| 3,593,709 A | 7/1971 | Halloran |
| 3,604,414 A | 9/1971 | Borges |
| 3,716,050 A | 2/1973 | Johnston |
| 3,741,205 A | 6/1973 | Markolf et al. |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,119,092 A | 10/1978 | Gil |
| 4,187,840 A | 2/1980 | Watanabe |
| 4,187,841 A | 2/1980 | Knutson |
| 4,201,215 A | 5/1980 | Crossett et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,457,307 A | 7/1984 | Stillwell |
| 4,484,570 A | 11/1984 | Sutter et al. |
| 4,493,317 A | 1/1985 | Klaue |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,867,144 A | 9/1989 | Karas et al. |
| 4,892,093 A | 1/1990 | Zarnowski et al. |
| 4,893,619 A | 1/1990 | Dale et al. |
| 4,903,691 A | 2/1990 | Heinl |
| 4,905,679 A | 3/1990 | Morgan |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,988,350 A | 1/1991 | Herzberg |
| 5,002,544 A | 3/1991 | Klaue et al. |
| 5,006,120 A | 4/1991 | Carter |
| 5,013,315 A | 5/1991 | Barrows |
| 5,015,248 A | 5/1991 | Burstein et al. |
| 5,021,056 A | 6/1991 | Hofmann et al. |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,129,899 A | 7/1992 | Small et al. |
| 5,133,718 A | 7/1992 | Mao |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,737 A | 4/1993 | Leibinger et al. |
| 5,234,431 A | 8/1993 | Keller |
| 5,254,119 A | 10/1993 | Schreiber |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,364,398 A | 11/1994 | Chapman et al. |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Du Toit |
| 5,423,826 A | 6/1995 | Coates et al. |
| 5,443,516 A | 8/1995 | Albrektsson et al. |
| 5,468,242 A | 11/1995 | Reisberg |
| 5,474,553 A | 12/1995 | Baumgart |
| 5,484,439 A | 1/1996 | Olson et al. |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Proctor et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,607,426 A | 3/1997 | Ralph et al. |
| 5,643,261 A | 7/1997 | Schafer et al. |
| 5,643,265 A | 7/1997 | Errico et al. |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,667 A | 10/1997 | Hausman |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |
| 5,904,683 A | 5/1999 | Pohndorf et al. |
| 5,916,216 A | 6/1999 | DeSatnick et al. |
| 5,919,195 A | 7/1999 | Wilson et al. |
| 5,928,234 A | 7/1999 | Manspeizer |
| 5,931,839 A | 8/1999 | Medoff |
| 5,938,664 A | 8/1999 | Winquist et al. |

| | | | | | |
|---|---|---|---|---|---|
| 5,941,878 A | 8/1999 | Medoff | 6,592,578 B2 | 7/2003 | Henniges et al. |
| 5,951,557 A | 9/1999 | Luter | 6,595,993 B2 | 7/2003 | Donno et al. |
| 5,954,722 A | 9/1999 | Bono | 6,602,255 B1 | 8/2003 | Campbell et al. |
| 5,964,763 A | 10/1999 | Incavo et al. | 6,623,486 B1 | 9/2003 | Weaver et al. |
| 5,968,046 A | 10/1999 | Castleman | 6,623,487 B1 | 9/2003 | Goshert |
| 5,968,047 A | 10/1999 | Reed | 6,669,731 B2 | 12/2003 | Ralph et al. |
| 5,973,223 A | 10/1999 | Tellman et al. | 6,682,531 B1 | 1/2004 | Winquist et al. |
| 6,001,099 A | 12/1999 | Huebner | 6,682,533 B1 | 1/2004 | Dinsdale et al. |
| 6,004,323 A | 12/1999 | Park et al. | 6,689,134 B2 | 2/2004 | Ralph et al. |
| 6,004,353 A | 12/1999 | Masini | 6,689,139 B2 | 2/2004 | Horn |
| 6,007,535 A | 12/1999 | Rayhack et al. | 6,695,846 B2 | 2/2004 | Richelsoph et al. |
| 6,022,350 A | 2/2000 | Ganem | 6,706,046 B2 | 3/2004 | Orbay et al. |
| 6,027,504 A | 2/2000 | McGuire | 6,712,820 B2 | 3/2004 | Orbay |
| 6,053,915 A | 4/2000 | Bruchmann | 6,719,759 B2 | 4/2004 | Wagner et al. |
| 6,077,266 A | 6/2000 | Medoff | 6,730,090 B2 | 5/2004 | Orbay et al. |
| 6,077,271 A | 6/2000 | Huebner et al. | 6,730,091 B1 | 5/2004 | Pfefferle et al. |
| 6,093,188 A | 7/2000 | Murray | 6,736,819 B2 | 5/2004 | Tipirneni |
| 6,096,040 A | 8/2000 | Esser | 6,767,351 B2 | 7/2004 | Orbay et al. |
| 6,113,603 A | 9/2000 | Medoff | 6,786,909 B1 | 9/2004 | Dransfeld et al. |
| 6,117,160 A | 9/2000 | Bonutti | 6,793,658 B2 | 9/2004 | LeHuec et al. |
| 6,123,709 A | 9/2000 | Jones | 6,821,278 B2 | 11/2004 | Frigg et al. |
| 6,129,728 A | 10/2000 | Schumacher et al. | 6,858,031 B2 | 2/2005 | Morrison et al. |
| 6,129,730 A | 10/2000 | Bono et al. | 6,866,665 B2 | 3/2005 | Orbay |
| 6,139,548 A | 10/2000 | Errico | 6,893,444 B2 | 5/2005 | Orbay |
| 6,152,927 A | 11/2000 | Farris et al. | 6,932,844 B2 | 8/2005 | Ralph et al. |
| 6,159,213 A | 12/2000 | Rogozinski | 6,955,677 B2 | 10/2005 | Dahners |
| 6,179,839 B1 | 1/2001 | Weiss et al. | 2001/0011172 A1 | 8/2001 | Orbay et al. |
| 6,183,475 B1 | 2/2001 | Lester et al. | 2002/0004660 A1 | 1/2002 | Henniges et al. |
| 6,193,721 B1 | 2/2001 | Michelson | 2002/0032446 A1 | 3/2002 | Orbay |
| 6,197,028 B1 | 3/2001 | Ray et al. | 2002/0055741 A1 | 5/2002 | Schlapfer et al. |
| 6,221,073 B1 | 4/2001 | Weiss et al. | 2002/0128654 A1 | 9/2002 | Steger et al. |
| 6,224,602 B1 | 5/2001 | Hayes | 2002/0143336 A1 | 10/2002 | Hearn |
| 6,228,087 B1 | 5/2001 | Fenaroli et al. | 2002/0143338 A1 | 10/2002 | Orbay et al. |
| 6,235,033 B1 | 5/2001 | Brace et al. | 2002/0147453 A1 | 10/2002 | Gambale |
| 6,235,034 B1 | 5/2001 | Bray | 2002/0151899 A1 | 10/2002 | Bailey et al. |
| 6,238,396 B1 | 5/2001 | Lombardo | 2002/0156474 A1 | 10/2002 | Wack et al. |
| 6,258,092 B1 | 7/2001 | Dall | 2002/0183752 A1 | 12/2002 | Steiner et al. |
| 6,261,291 B1 | 7/2001 | Talaber et al. | 2003/0040748 A1 | 2/2003 | Aikins et al. |
| 6,273,889 B1 | 8/2001 | Richelsoph | 2003/0055429 A1 | 3/2003 | Ip et al. |
| 6,283,969 B1 | 9/2001 | Grusin et al. | 2003/0105461 A1 | 6/2003 | Putnam |
| 6,290,703 B1 | 9/2001 | Ganem | 2003/0149434 A1 | 8/2003 | Paul |
| 6,302,883 B1 | 10/2001 | Bono | 2003/0153918 A1 | 8/2003 | Putnam et al. |
| 6,302,884 B1 | 10/2001 | Wellisz et al. | 2003/0233093 A1 | 12/2003 | Moles et al. |
| 6,302,887 B1 | 10/2001 | Spranza et al. | 2004/0102775 A1 | 5/2004 | Huebner |
| 6,306,136 B1 | 10/2001 | Baccelli | 2004/0102776 A1 | 5/2004 | Huebner |
| 6,312,431 B1 | 11/2001 | Asfora | 2004/0102777 A1 | 5/2004 | Huebner |
| 6,315,779 B1 | 11/2001 | Morrison et al. | 2004/0102778 A1 | 5/2004 | Huebner et al. |
| 6,322,562 B1 | 11/2001 | Wolter | 2004/0116930 A1 | 6/2004 | O'Driscoll et al. |
| 6,325,803 B1 | 12/2001 | Schumacher et al. | 2004/0122429 A1 | 6/2004 | Phillips et al. |
| 6,331,179 B1 | 12/2001 | Freid et al. | 2004/0127901 A1 | 7/2004 | Huebner et al. |
| 6,336,927 B2 | 1/2002 | Rogozinski | 2004/0127903 A1 | 7/2004 | Schlapfer et al. |
| 6,338,734 B1 | 1/2002 | Burke et al. | 2004/0153073 A1 | 8/2004 | Orbay |
| 6,342,055 B1 | 1/2002 | Eisermann et al. | 2004/0167522 A1 | 8/2004 | Niederberger et al. |
| 6,342,075 B1 | 1/2002 | MacArthur | 2004/0193164 A1 | 9/2004 | Orbay |
| 6,355,036 B1 | 3/2002 | Nakajima | 2004/0193165 A1 | 9/2004 | Orbay |
| 6,355,042 B2 | 3/2002 | Winquist | 2004/0210220 A1 | 10/2004 | Tornier |
| 6,358,250 B1 | 3/2002 | Orbay | 2004/0220566 A1 | 11/2004 | Bray |
| 6,364,881 B1 | 4/2002 | Apgar et al. | 2004/0225291 A1 | 11/2004 | Schwammberger et al. |
| 6,364,882 B1 | 4/2002 | Orbay | 2004/0260291 A1 | 12/2004 | Jensen |
| 6,364,883 B1 | 4/2002 | Santilli | 2004/0260292 A1 | 12/2004 | Orbay et al. |
| 6,379,354 B1 | 4/2002 | Rogozinski | 2004/0260293 A1 | 12/2004 | Orbay et al. |
| 6,379,364 B1 | 4/2002 | Brace et al. | 2004/0260294 A1 | 12/2004 | Orbay et al. |
| 6,402,756 B1 | 6/2002 | Ralph et al. | 2004/0260295 A1 | 12/2004 | Orbay et al. |
| 6,413,259 B1 | 7/2002 | Lyons et al. | 2005/0015089 A1 | 1/2005 | Young et al. |
| 6,428,542 B1 | 8/2002 | Michelson | 2005/0049593 A1 | 3/2005 | Duong et al. |
| 6,436,103 B1 | 8/2002 | Suddaby | 2005/0049594 A1 | 3/2005 | Wack et al. |
| 6,440,135 B2 | 8/2002 | Orbay et al. | 2005/0065520 A1 | 3/2005 | Orbay |
| 6,454,769 B2 | 9/2002 | Wagner et al. | 2005/0065522 A1 | 3/2005 | Orbay |
| 6,454,770 B1 | 9/2002 | Klaue | 2005/0065523 A1 | 3/2005 | Orbay |
| 6,458,133 B1 | 10/2002 | Lin | 2005/0065524 A1 | 3/2005 | Orbay |
| 6,468,278 B1 | 10/2002 | Muckter | 2005/0065528 A1 | 3/2005 | Orbay |
| 6,503,250 B2 | 1/2003 | Paul | 2005/0085818 A1 | 4/2005 | Huebner |
| 6,508,819 B1 | 1/2003 | Orbay | 2005/0085819 A1 | 4/2005 | Ellis et al. |
| 6,514,274 B1 | 2/2003 | Boucher et al. | 2005/0131413 A1 | 6/2005 | O'Driscoll et al. |
| 6,520,965 B2 | 2/2003 | Chervitz et al. | 2005/0159747 A1 | 7/2005 | Orbay |
| 6,527,775 B1 | 3/2003 | Warburton | 2005/0165395 A1 | 7/2005 | Orbay et al. |
| 6,533,789 B1 | 3/2003 | Hall, IV et al. | 2005/0165400 A1 | 7/2005 | Fernandez |
| 6,547,790 B2 | 4/2003 | Harkey et al. | 2005/0171544 A1 | 8/2005 | Falkner |
| 6,565,570 B2 | 5/2003 | Sterett et al. | 2005/0182405 A1 | 8/2005 | Orbay et al. |

| | | | |
|---|---|---|---|
| 2005/0182406 | A1 | 8/2005 | Orbay et al. |
| 2005/0187551 | A1 | 8/2005 | Orbay et al. |
| 2005/0192578 | A1 | 9/2005 | Horst |
| 2005/0234458 | A1 | 10/2005 | Huebner |
| 2007/0185493 | A1 | 8/2007 | Feibel et al. |

FOREIGN PATENT DOCUMENTS

| | | |
|---|---|---|
| CH | 611147 | 5/1979 |
| DE | 2515430 | 11/1975 |
| DE | 4201531 | 7/1993 |
| DE | 4343117 | 6/1995 |
| EP | 0053999 | 6/1982 |
| EP | 0410309 | 1/1991 |
| EP | 0415837 | 3/1991 |
| EP | 0471418 | 2/1992 |
| EP | 0362049 | 5/1992 |
| EP | 1250892 | 9/2003 |
| FR | 742.618 | 3/1933 |
| FR | 2254298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 | 2/1992 |
| SU | 1734715 | 5/1992 |
| WO | 82/01645 | 5/1982 |
| WO | 87/02572 | 5/1987 |
| WO | 88/03781 | 6/1988 |
| WO | 96/29948 | 10/1996 |
| WO | 97/47251 | 12/1997 |
| WO | 01/21083 | 3/2001 |
| WO | 01/62136 | 8/2001 |
| WO | 03/105712 | 12/2003 |

OTHER PUBLICATIONS

Ace Medical Company, Ace 4.5/5.0 mm Titanium Cannulated Screw and Reconstruction Plate System simplified fracture fixation brochure, 1992.
Ace Medical Company, Ace 4.5/5.0 mm Titanium Cannulated Screw and Reconstruction Plate System surgical technique brochure, 1992.
Ace Medical Company, Ace Symmetry Titanium Upper Extremity Plates surgical technique brochure, 1996.
Ace Medical Company, Ace Titanium 3.5/4.0 mm Screw and Plate System with the Ace 3.5 mm Universal Ribbon CT/MRI compatible fixation brochure, 1992.
Ace Medical Company, The Ace Symmetry Titanium Upper Extremity Plates new product release brochure, 1996.
Acumed Inc., Congruent Distal Radius Plate System description, Mar. 4, 1998.
Acumed Inc., Congruent Plate System—The Mayo Clinic Congruent Elbow Plates brochure, May 7, 2002.
Acumed Inc., Modular Hand System brochure, Aug. 2002.
Acumed Inc., Modular Hand System brochure, Sep. 2002.
Amadio, Open Reduction of Intra-Articular Fractures of the Distal Radius, *Fractures of the Distal Radius*, pp. 193-202, 1995.
An, Y.H., *Internal Fixation in Osteoporotic Bone*, pp. 82-83, 2002.
Avanta Orthopaedics, SCS/D Distal Radius Plate System brochure, 1997.
Avanta Orthopaedics, SCS/V Distal Radius Plate Volar brochure, 1998.

Beaupre et al., A Comparison of Unicortical and Bicortical End Screw Attachment of Fracture Fixation Plates, *Journal of Orthopaedic Trauma*, vol. 6, No. 3, pp. 294-300, 1992.
Biomet Orthopedics, Inc., Supracondylar Cable Plate brochure, 2000.
Chin et al., Salvage of Distal Tibia Metaphyseal Nonunions With the 90° Cannulated Blade Plate, *Clinical Orthopaedics and Related Research*, No. 409, pp. 241-249, 2003.
DePuy Ace Medical Company, *TiMAX Pe.R.I. Small Fragment Upper Extremity* description pages, 1999.
DePuy, Inc., McBride S.M.O. Stainless Steel Bone Plates brochure, 1943.
DuCloyer, *Treatment by Plates of Anteriorly Displaced Distal Radial Fractures*, Fractures of the Distal Radius, pp. 148-152, 1995.
DVO Extremity Solutions, MIfx Dorsal IM Plate, brochure, Sep. 2005.
Erothitan Titanimplantate AG, Titanium Wire Plate Osteosynthesis System According to Dr. Gahr internet printout, print date Feb. 6, 2003.
Esser, Treatment of Three- and Four-Part Fractures of the Proximal Humerus with a Modified Cloverleaf Plate, *Journal of Orthopaedic Trauma*, vol. 8, No. 1, pp. 15-22, 1994.
Fernandez et al., *Fractures of the Distal Radius: A Practical Approach to Management*, pp. 103-188, 1996.
Fitoussi et al., Treatment of Displaced Intra-Articular Fractures of the Distal End of the Radius With Plates, *The Journal of Bone and Joint Surgery*, vol. 79, No. 9, pp. 1303-1312, 1997 (abstract only provided).
Gesensway et al., Design and Biomechanics of a Plate for the Distal Radius, *Journal of Hand Surgery*, vol. 20, No. 6, pp. 1021-1027, 1995 (abstract only provided).
Harvey et al., The Use of a Locking Custom Contoured Blade Plate for Peri-Articular Nonunions, *Injury, Int. J. Care Injured*, vol. 34, pp. 111-116, 2003.
Hooker et al., *Fixation of Unstable Fractures of the Volar Rim of the Distal Radius with a Volar Buttress Pin®*, 2003.
Howmedica Inc., Dupont Distal Humeral Plates brochure, 1990.
Jupiter et al., Management of Comminuted Distal Radial Fractures, *Fractures of the Distal Radius*, pp. 167-183, 1995.
Kambouroglou et al, Complications of the AO/ASIF Titanium Distal Radius Plate System (π Plate) in Internal Fixation of the Distal Radius: A Brief Report, *Journal of Hand Surgery*, vol. 23A, No. 4, pp. 737-741, Jul. 1998.
Kolodziej et al., Biomechanical Evaluation of the Schuhli Nut, *Clinical Orthopaedics and Related Research*, vol. 347, pp. 79-85, Feb. 1998.
Konrath et al., Open Reduction and Internal Fixation of Unstable Distal Radius Fractures: Results Using the Trimed Fixation System, *Journal of Orthopaedic Trauma*, vol. 16, No. 8, pp. 578-585, 2002.
Leung et al., Palmar Plate Fixation of AO Type C2 Fracture of Distal Radius Using a Locking Compression Plate—A Biomechanical Study in a Cadaveric Model, *Journal of Hand Surgery*, vol. 28B, No. 3, pp. 263-266, Jun. 2003.
Martin GmbH & Co. KG, Bilder internet printout, print date Sep. 5, 2003.
Mizuho Co., Ltd., Jplate Diaphysis Plates for Japanese brochure, 2002.
Morgan et al., Salvage of Tibial Pilon Fractures Using Fusion of the Ankle with a 90° Cannulated Blade Plate: A Preliminary Report, *Foot & Ankle International*, vol. 20, No. 6, pp. 375-378, Jun. 1999.
Nunley et al., Delayed Rupture of the Flexor Pollicis Longus Tendon After Innappropriate Placement of the π Plate on the Volar Surface of the Distal Radius, *Journal of Hand Surgery*, vol. 24, No. 6, pp. 1279-1280, Nov. 1999.
Orthocopia, LLC, Synthes Volar Distal Radius Locking Plate internet description page, 2004.
Osada et al., Comparison of Different Distal Radius Dorsal and Volar Fracture Fixation Plates: A Biomechanical Study, *Journal of Hand Surgery*, vol. 28A, No. 1, pp. 94-104, Jan. 2003.
Palmer et al., The Use of Interlocked 'Customised' Blade Plates in the Treatment of Metaphyseal Fractures in Patients with Poor Bone Stock, *Injury, Int. J. Care Injured*, vol. 31, pp. 187-191, 2002.

Peine et al., Comparison of Three Different Plating Techniques for the Dorsum of the Distal Radius: A Biomechanical Study, *Journal of Hand Surgery*, vol. 25A, No. 1, pp. 29-33, Jan. 2000.

Putnam et al., Distal Radial Metaphyseal Forces in an Extrinsic Grip Model: Implications for Postfracture Rehabilitation, *Journal of Hand Surgery*, vol. 25A, No. 3, pp. 469-475, May 2000.

Reip, David, Authorized officer, International Searching Authority, International Search Report for PCT Patent Application Serial No. PCT/US2003/22904, Dec. 4, 2003.

Ring et al., Prospective Multicenter Trial of a Plate for Dorsal Fixation of Distal Radius Fractures, *The Journal of Hand Surgery*, vol. 22A, No. 5, pp. 777-784, Sep. 1997.

Rozental et al., Functional Outcome and Complications Following Two Types of Dorsal Plating for Unstable Fractures of the Distal Part of the Radius, *Journal of Bone and Joint Surgery*, vol. 85, No. 10, pp. 1956-1960, 2003 (abstract only).

Ruch et al., Results of Palmar Plating of the Lunate Facet Combined with External Fixation for the Treatment of High-Energy Compression Fractures of the Distal Radius, *J. Orthop. Trauma*, Vo. 18, No. 1, pp. 28-33, Jan. 2004.

Sanatmetal, *Rib Securing Clamped Plate*, internet printout, Sep. 2004 <http://www.sanatmetal.hu/catalog/pict/1_5_89a_1.jpg>.

Sanchez-Sotelo et al., Principle-Based Internal Fixation of Distal Humerus Fractures, *Techniques in Hand & Upper Extremity Surgery*, vol. 5, No. 4, pp. 179-187, Dec. 2001.

Simic, Fractures of the Distal Aspect of the Radius: Changes in Treatment Over the Past Two Decades, *Journal of Bone and Joint Surgery*, vol. 85-A, No. 3, pp. 552-564, Mar. 2003.

Stryker SmartLock Locking Screw Technology, advertisement, *The Journal of Hand Surgery*, vol. 30A, No. 1, Jan. 2005.

Surfix Technologies, Single Units Osteosynthesis brochure, Sep. 2000.

Synthes (USA), 3.5 mm LCP™ Proximal Humerus Plate technique guide, 2002.

Synthes (USA), *Biological Plating: A New Concept to Foster Bone Healing*, 1991.

Synthes (USA), The Distal Radius Plate Instrument and Implant Set technique guide, 1999.

Synthes (USA), The Titanium Distal Radius Plate, technique guide, 1997.

Synthes (USA), Titanium Distal Radius Plates description page, 2001.

Synthes, Small Titanium Plates overview page, p. 2a-33, Mar. 1997.

Synthes, Titanium Distal Radius Instrument and Implant Set standard contents description pages, Mar. 1997.

Techmedica, Inc., Techmedica Bioengineers Keep Tabs on Your Needs brochure, 1991.

Techmedica, Inc., The Arnett-TMP Titanium Miniplating System brochure, 1989.

Toby, *Scaphoid Protocols Using the Acutrak® Bone Screw System* brochure, published by Acumed, Inc., Dec. 7, 1999.

Tornetta, Distal Radius Fracture, *Journal of Orthopaedic Trauma*, vol. 16, No. 8, pp. 608-611, 2002.

Trimed Inc., *TriMed Wrist Fixation System* brochure, 1997.

Trimed Inc., *TriMed Wrist Fixation System* internet description pages, 2001.

Trumble et al., Intra-Articular Fractures of the Distal Aspect of the Radius, *Journal of Bone and Joint Surgery*, vol. 80A, No. 4, pp. 582-600, Apr. 1998.

Turner et al., *Tendon Function and Morphology Related to Material and Design of Plates for Distal Radius Fracture Fixation: Canine Forelimb Model*, Orthopaedic Research Society, Feb. 2003.

Vitallium, Bone Plates brochure, Mar. 1948.

Waldemar Link GmbH & Co., May Anatomical Bone Plates: Plates, Bone Screws and Instruments brochure, pp. 3-4 and 10-15, 1995.

Wright Medical Technology, Inc., Locon-T Distal Radius Plating System brochure, 2002.

Wright Medical Technology, Inc., Locon-T Distal Radius Plating System case study and surgical method, 2001.

Young, Outcome Following Nonoperative Treatment of Displaces Distal Radius Fractures in Low-Demand Patients Older Than 60 Years, *Journal of Hand Surgery*, vol. 25A, No. 1, pp. 19-28, Jan. 2000.

Zespol Bone Plates, in *Mikromed—Catalogue 2004* (Nov. 2004), original website <http://www.mikromed.pl/katalog/Main/main_eng.htm> and < http://www.mikromed.pl/katalog/zespol_eng/plytki.htm >, viewable via the Internet Archive Wayback Machine < http://replay.waybackmachine.org/20070830023439/http://www.mikromed.pl/katalog/zespol_eng/plytki.htm >.

Zespol Bone Screws, in *Mikromed—Catalogue 2004* (Nov. 2004), original website <http://www.mikromed.pl/katalog/Main/main_eng.htm> and < http://www.mikromed.pl/katalog/zespol_eng/wkrety.htm >, viewable via the Internet Archive Wayback Machine < http://replay.waybackmachine.org/20050226124226/http://www.mikromed.pl/katalog/zespol_eng/wkrety.htm >.

Zimmer, Inc., Forte Distal Radial Plate System brochure, 1995.

Zimmer, Inc., Periarticular Plating System brochure, 2002.

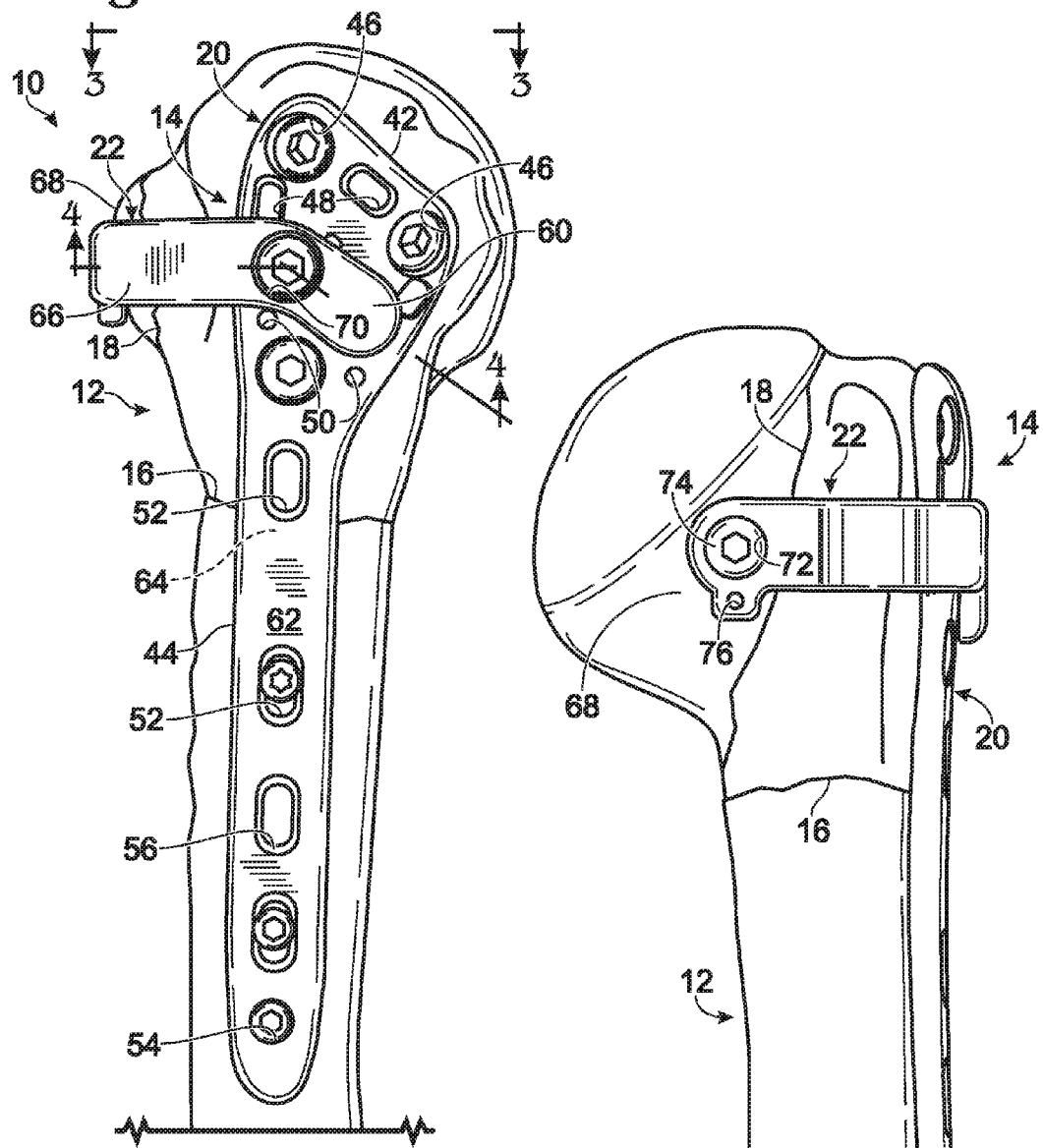
Fig. 1

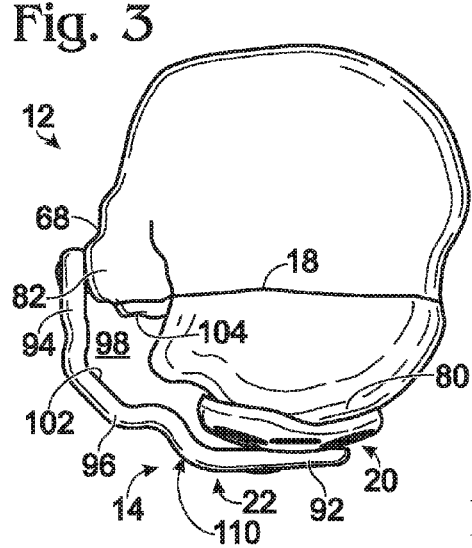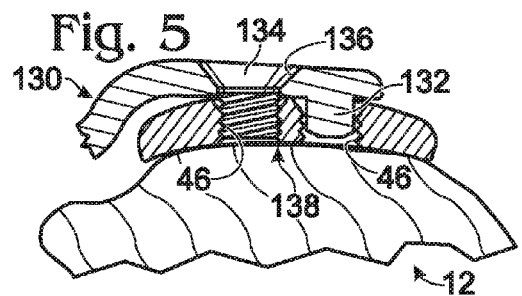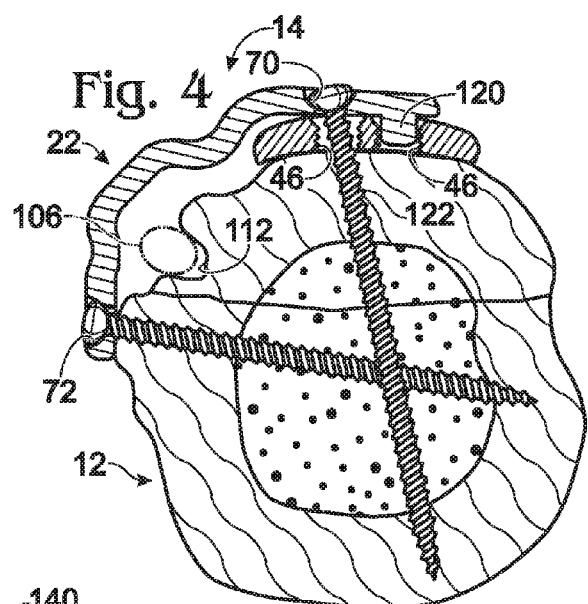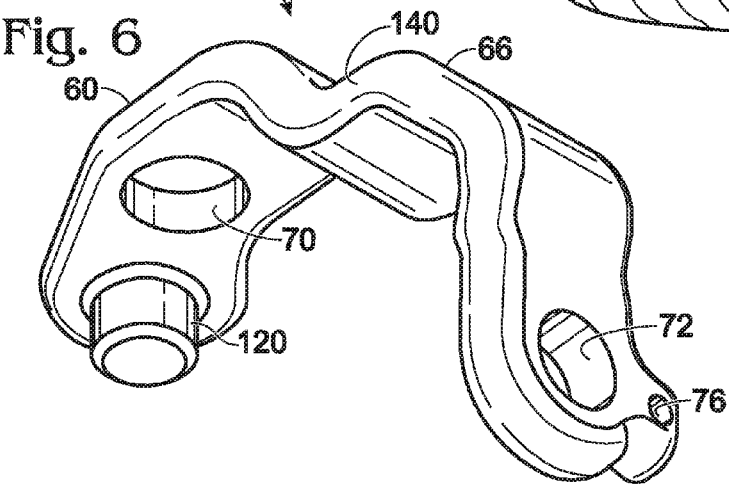

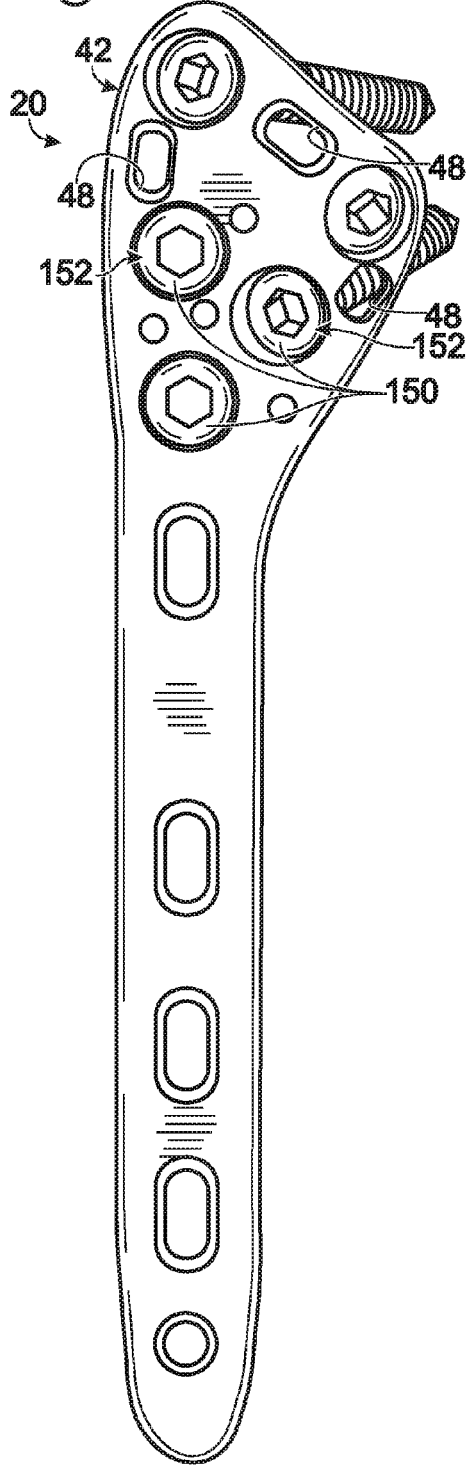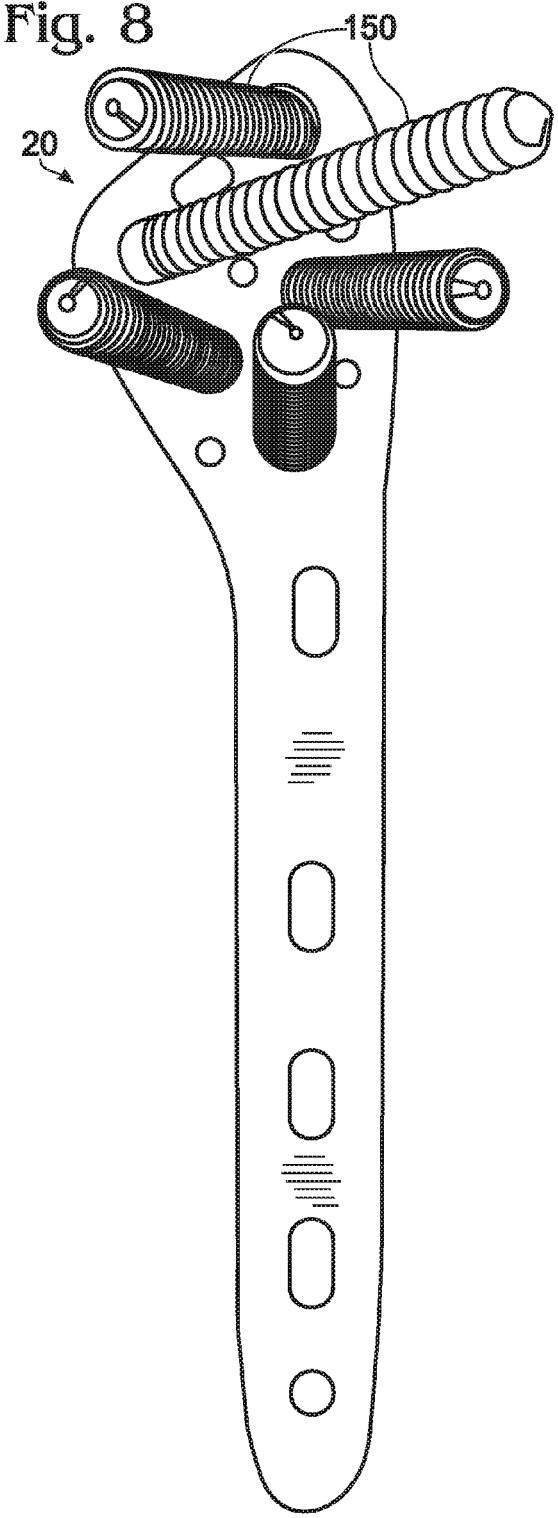

EXPANDED FIXATION OF BONES

CROSS-REFERENCE TO PRIORITY APPLICATIONS

This application is a continuation of U.S. patent application Ser. No. 11/112,858, filed Apr. 22, 2005, which in turn is based upon and claims the benefit under 35 U.S.C. §119(e) of U.S. Provisional Patent Application Ser. No. 60/564,853, filed Apr. 22, 2004. Each of these priority applications is incorporated herein by reference in its entirety for all purposes.

CROSS-REFERENCE TO RELATED APPLICATION

This application incorporates herein by reference U.S. patent application Ser. No. 11/109,985, filed Apr. 19, 2005, now abandoned.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become damaged should be repaired promptly and properly. Typically, a fractured or cut bone is treated using a fixation device, which reinforces the bone and keeps it aligned during healing. Fixation devices may include external fixation devices (such as casts and/or fixators) and/or internal fixation devices (such as bone plates, rods, and/or bone screws), among others.

Bone plates are sturdy internal devices, usually made of metal, that mount directly to the bone adjacent a fracture (or other bone discontinuity). To use a bone plate to repair a bone discontinuity, a surgeon typically (1) selects an appropriate bone plate, (2) reduces the discontinuity (e.g., sets the fracture), and (3) fastens the bone plate to bone fragments disposed on opposite sides of the discontinuity using suitable fasteners, such as screws and/or wires, so that the bone plate spans the discontinuity and the bone fragments are fixed in position.

Standard bone plates and their associated fasteners may be insufficient to fix some orthopedic injuries in which bones are broken into several pieces. For example, a bone plate disposed axially on a multiply fractured humerus, so that the bone plate spans and fixes a generally transverse fracture of the humerus, may not be capable of also spanning and fixing various oblique or axial fractures of this bone. This problem may be exacerbated further by bone plates that are pre-shaped to fit onto a particular region of a target bone.

SUMMARY

The present teachings provide a system, including methods, apparatus, and kits, for expanded bone fixation with bone plates.

BRIEF DESCRIPTION OF THE DRAWINGS

FIG. 1 is a lateral view of an exemplary system for expanded bone fixation including a left humerus fractured proximally and fixed with a bone plate and an extension member secured to the bone plate, in accordance with aspects of the present teachings.

FIG. 2 is an anterior view of the system of FIG. 1.

FIG. 3 is a superior view of the system of FIG. 1, taken generally along line 3-3 of FIG. 1.

FIG. 4 is a sectional view of the system of FIG. 1, taken generally along line 4-4 of FIG. 1.

FIG. 5 is a fragmentary sectional view of the bone plate and left humerus of FIG. 1, taken generally as in FIG. 4, with another exemplary extension member secured to the bone plate using a coupling mechanism distinct from that of FIG. 4, in accordance with aspects of the present teachings.

FIG. 6 is a view of the extension member of FIG. 1 in the absence of the bone plate and bone.

FIG. 7 is a view of the bone plate of FIG. 1, taken generally toward the outer surface of the bone plate, with a head portion of the bone plate in threaded engagement with bone screws and in the absence of the extension member and bone, in accordance with aspects of the present teachings.

FIG. 8 is a view of the bone plate and bone screws of FIG. 7, taken generally toward the inner surface of the bone plate, in accordance with aspects of the present teachings.

DETAILED DESCRIPTION

The present teachings provide a system, including methods, apparatus, and kits, for expanded fixation with bone plates. The bone plates may include and/or may be coupled to an extension member (e.g., a plate member) that enlarges the footprint of the bone plates on bone, such as the footprint on a proximal region of a humerus bone.

The extension member may be formed integrally with the bone plate or may be attached volitionally (and optionally) to the bone plate before, during, and/or after the bone plate is secured to bone. The extension member thus may extend to and may be secured to a bone surface region that is spaced from the bone plate, for example, a bone surface region that is disposed axially, laterally, and/or partway around the bone from the footprint of the bone plate on bone. In some examples, the extension member may have opposing end regions that respectively engage a bone plate and bone, and an intermediate region that is spaced from bone, to, for example, accommodate soft tissue disposed between the intermediate region and bone. Overall, the system described herein may increase the functionality of bone plates, for example, by expanding the ability of the bone plates to span discontinuities and/or to reinforce bone.

FIG. 1 shows an exemplary system 10 for expanded bone fixation. The system may include a bone, such as a left humerus bone 12, and a fixation device 14 secured to and reinforcing the bone. The fixation device may span one or more discontinuities in the bone. For example, the fixation device may span a transverse fracture (or other transverse discontinuity) 16 and/or an additional fracture (or other additional discontinuity) 18 (e.g., a fracture that extends obliquely and/or axially in the bone). The fixation device may include a bone plate 20 and an extension member 22 (e.g., an extension plate) secured to (and/or unitary with) the bone plate. The bone plate and extension member may have any suitable relative orientations. In some examples, the bone plate may extend generally along the bone, to span the transverse discontinuity and stabilize the bone with respect to the transverse discontinuity (but generally not substantially with respect to the additional discontinuity). The extension member may extend partially around the bone, to span the additional discontinuity and stabilize the bone with respect to the additional discontinuity and thus expand the fixation capability of the bone plate. The bone plate and/or extension member may include openings that receive fasteners, such as bone screws, to secure the bone plate and/or extension member to bone and/or to each other.

The following sections describe further aspects of the present teachings, including, among others, (I) bone plates, (II) extension members, (III) methods of fixing bones using bone plates and extension members, (IV) kits, and (V) examples.

I. BONE PLATES

Bone plates as described herein generally comprise any relatively low-profile (or plate-like) fixation device configured to stabilize at least one bone by attachment to the bone. The fixation device may be configured to span any suitable bone discontinuity (or discontinuities) so that the fixation device fixes the relative positions of bone fragments (and/or bones) disposed on opposing sides of the bone discontinuity (or discontinuities). Alternatively, or in addition, the fixation device may reinforce a bone lacking a discontinuity.

Suitable discontinuities may occur naturally and/or may result from injury, disease, and/or surgical intervention, among others. Accordingly, exemplary discontinuities for use with the fixation devices described herein may include joints, fractures (breaks in bones), osteotomies (cuts in bones), and/or nonunions (for example, produced by injury, disease, or a birth defect), among others.

The bone plates described herein may be configured for use on any suitable bone, in any suitable animal species, including human, equine, canine, and feline species, among others. Exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, ribs, and/or clavicles, among others. Particular exemplary regions of bones where the bone plates described herein may be secured include a proximal portion and/or a lateral surface of the humerus bone. Particular fractures where the bone plates described herein may be suitable include bones with multiple fractures creating a plurality of bone fragments. One or more of the fragments may not be suitably disposed for securing directly and/or sufficiently to a bone plate with a fastener placed through an opening of the bone plate and into the fragment because of, for example, the size, position, structure, etc., of the one or more fragments.

Each bone plate may be configured to be disposed in any suitable position relative to its target bone. The bone plate (or a plate portion) may be configured to be disposed in contact with an exterior surface of the bone and thus may be positioned at least substantially (or completely) exterior to the bone. Alternatively, the bone plate may be configured to be disposed at least partially interior to a bone, that is, apposed to (normally) interior bone surfaces when secured to the bone. The interior surfaces of the bone may be accessed during installation of the bone plate (such as by punching the bone plate through the exterior bone surface) and/or may be accessible due to a break, a cut, and/or the like.

The bone plates may be formed of any suitable material(s). The bone plates may be of a sturdy yet malleable construction. Generally, the bone plates should be stiffer and stronger than the section of bone spanned by the plates, yet flexible (e.g., springy) enough not to strain the bone significantly. A bone plate of the present teachings may be at least substantially formed of, or may include, any suitable biocompatible material(s) and/or bioresorbable material(s). Exemplary biocompatible materials that may be suitable for the bone plate include (1) metals/metal alloys (for example, titanium or titanium alloys, alloys with cobalt and chromium (such as cobalt-chrome), stainless steel, etc.); (2) plastics (for example, ultra-high molecular weight polyethylene (UHM-WPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites (for example, carbon-fiber composites); (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); and/or the like. In some examples, one or more of these materials may form the body of a bone plate and/or a coating thereon.

The bone plates may be configured to reduce irritation to the bone and surrounding tissue. For example, the bone plates may be formed of a biocompatible material, as described above. In addition, the bone plates may have a low and/or feathered profile to reduce their protrusion into adjacent tissue and rounded, burr-free surfaces to reduce the effects of such protrusion.

The bone plates described herein may be sized and shaped to conform to particular portions of a bone (or bones). The plates may be generally elongate, with a length L, a width W, and a thickness T. Here, length L≧width W>thickness T. In use, the long axis of the bone plates (or of a plate portion) may be aligned with the long axis of the corresponding bone, and/or may extend obliquely and/or transversely relative to the bone's long axis. The length and/or width of the bone plates may be varied according to the intended use, for example, to match the plates with a preselected region of bone(s) and/or a particular injury to the bone. For example, the plates may be generally linear for use on the shaft of a long bone and/or may have a nonlinear shape, such as for use near an end of a bone and/or for transverse placement on the shaft, among others. In some examples, the bone plates (and/or extension members) may be configured to wrap at least partially around a bone, so that portions of each plate (and/or extension member) are disposed on distinct sides and/or generally opposing sides/surfaces of a bone. In some embodiments, the bone plates may be configured for use on both sides of the body/skeleton, such as when the bone plates are bilaterally symmetrical. In some embodiments, the bone plates may be asymmetrical and configured for use on either the left or the right side of the body/skeleton, but not both.

The bone plates may include inner (bone-facing) and outer (bone-opposing) surfaces. One or both of these surfaces may be contoured generally to follow an exterior surface of a target bone (or bones) for which a bone plate is intended, so that the bone plate maintains a low profile and fits onto the bone(s). For example, the inner surface of a plate may be generally complementary in contour to the bone surface. The outer surface of the plate also may correspond in contour to the bone surface and may be generally complementary to the inner surface of the plate. The bone plates may be partially and/or completely precontoured, at the time of manufacture, allowing practitioners to apply them to bone(s) with little or no additional bending at the time of application. Alternatively, or in addition, the bone plates may be custom-contoured by practitioners before and/or during installation onto bone.

The thickness of the bone plates may be defined by the distance between the inner and outer surfaces of the plates. The thickness of the plates may vary between plates and/or within the plates, according to the intended use. For example, thinner plates may be configured for use on smaller bones and/or on bones or bone regions where soft tissue irritation is a greater concern. Thickness may be varied within the plates. For example, the plates may become thinner as they extend over protrusions (such as processes, condyles, tuberosities, and/or the like), reducing their profile and/or rigidity, among others. Alternatively, or in addition, the thickness may vary as an interior portion of the bone plate extends into bone, for example, becoming thinner to facilitate insertion of this interior portion or thicker to increase structural stability. The thickness of the plates also may be varied to facilitate use, for example, to make the plates thinner where they typically need to be deformed by bending and/or twisting the plates, such as at a junction (or bridge region) between plate portions. In this way, the plates may be thicker and thus stronger in regions where they may not need to be contoured, such as along the shaft of the bone. In some examples, the inner and/or outer surface of a bone plate may define a recess in which an extension plate may be received. This recess may reduce the profile of the extension plate above (or below) the bone plate.

The bone plates generally include a plurality of openings. The openings may be adapted to receive fasteners for securing the plates to bone. Alternatively, or in addition, one or more of the openings may be configured to alter the local rigidity of the plates, to permit the plates to be manipulated with a tool (such as an attachable handle), to facilitate blood flow to bone regions where the bone plates are installed, to promote healing, and/or the like. In some examples, one or more of the openings may be adapted to receive a fastener that attaches the plate to a corresponding extension member and/or to receive a projection of the extension member. These openings may extend through the bone plates (between inner and outer surfaces) and/or may extend at least substantially parallel to the inner and/or outer surfaces of the bone plates.

The openings may have any suitable positions, sizes, and/or densities within each portion of a bone plate. The openings may be arrayed generally in a line along a portion of the plate, for example, centered across the width of the plate. Alternatively, the openings may be arranged nonlinearly, for example, disposed in an arcuate, staggered, or other two-dimensional (or three-dimensional) arrangement.

The openings may have any suitable shape and structure. Exemplary shapes may include circular, elongate (such as elliptical, rectangular, oval), etc. The openings may include counterbores. The counterbores may be configured, for example, to receive a head of a bone screw, to reduce or eliminate protrusion of the head above the outer surface of the plate. The openings may be threaded or nonthreaded, and each bone plate may include one or more threaded and/or nonthreaded openings. In some embodiments, the plates may include one or a plurality of elongate openings (for example, oval openings) extending axially, obliquely, and/or transversely within each bone plate. The elongate openings may be compression slots that include contoured counterbores to provide compression when heads of bone screws are advanced against the counterbores. Alternatively, or in addition, the elongate openings may be used to adjust the position of bone plates and/or plate portions relative to bone before the plates are fully secured to the bone.

In some examples, the bone plates may include one or more projections. The projections may extend, for example generally orthogonal from the inner surface of the bone plates toward bone. Alternatively, or in addition, the projections may extend generally outward from the outer surface of the bone plates. In either configuration, the projections may be configured to engage corresponding openings of extension members. The projections may be sharp or blunt according to their intended use. For examples, sharp projections may be configured as prongs that penetrate bone to restrict movement of the bone plates. Prongs may be used in place of, or in addition to, bone fasteners, for one or more portions of each bone plate. Blunt (or sharp) projections, such as ridges or knobs (or tines), may be configured for mating with openings/depressions of extension members or as spacing members that elevate the bone plates from the bone surface.

The bone plates may have at least one, and generally two or more, plate portions (or anchor portions) configured to be secured to different regions of a bone (or bones). Each plate portion may be structured for a specific region of a bone. For example, the bone plates may include a proximal plate portion for attachment to a more proximal region of a bone, and a distal plate portion for attachment to a more distal region of the same bone. Alternatively, or in addition, the bone plates may include an exterior plate portion configured to fit against an exterior surface region of bone adjacent a bone discontinuity, and/or an interior plate portion configured to be received in an interior (e.g., recessed, resected, and/or excavated) region of bone adjacent the bone discontinuity.

The plate portions of a bone plate may have any suitable connection. In some examples, the plate portions may be formed integrally, so that one piece of the bone plate includes the plate portions. Alternatively, plate portions may be formed as separate pieces. The separate pieces may be connected by any suitable connection and/or joint, including a fastener(s), welding, a hinge joint, a ball-in-socket joint, and/or the like. Further aspects of bone plates having adjustable joints are described in the following patent application, which is incorporated herein by reference: U.S. patent application Ser. No. 10/716,719, filed Nov. 19, 2003.

The plate portions of a bone plate may have any suitable relative disposition. The plate portions may be disposed such that they are substantially collinear and/or parallel, oblique, or substantially transverse to one another. The relative disposition may be fixed and/or adjustable. In some examples, the plate portions may be connected integrally by a deformable bridge region, so that the bone plate can be bent pre- and/or peri-operatively to adjust the relative disposition of the plate portions. Alternatively, the plate portions may be distinct pieces connected, for example, through an adjustable joint, as described above.

Each plate portion may have one or more openings and/or other receiving structures. Each opening may be configured to receive a fastener for placement of the bone fastener into bone and/or for connection of the plate portion to an extension member.

II. EXTENSION MEMBERS

Each fixation device may include an extension member (or a plurality of extension members) joined to and/or securable to a bone plate. The extension member may include any support structure that extends beyond the perimeter of the bone plate to increase the footprint of the bone plate on bone. The extension member may be configured as an ancillary plate member or a plate portion for a bone plate. Accordingly, the extension member may have any of the properties described above for bone plates. Alternatively, the extension member may have comparable cross-sectional dimensions such that the extension member includes a wire or a wire-like structure.

The extension member may have any suitable shape. The extension member may be configured to be plate-like, so that the extension member may have a length and a width that are substantially greater than the thickness of the extension member. The extension member may be elongate or may have a length that is approximately equal to the width of the extension member. The extension member may have a contour that conforms generally to the contour of a bone surface onto which the extension member fits, so that the extension member generally follows the bone surface. However, in some examples, the extension member may be contoured also or alternatively to extend over a (non-bone) soft tissue structure, such as a tendon or a muscle. In exemplary embodiments, the extension member may be configured to extend over the biceps tendon disposed in the bicipital groove of the humerus (see Example 1). In some examples, the bone plate may be configured to be secured adjacent (and/or engage) the outer surface (or inner surface) of a bone plate, and thus may be configured to bend toward (or away from) bone as the extension member extends beyond the bone plate perimeter, to reduce (or increase) the profile of the extension member. In some examples, the bone plate and the extension member may be or may include elongate portions, disposed in use in substantially transverse directions (at least near their point(s) of contact with one another). For example, the bone plate may have a long axis that is aligned generally with a long axis of a bone, and the extension member(s) may include a curved portion that forms an arm that extends in use at least partially around rather than along a bone.

The extension member may have any suitable size. The extension member may be configured to extend any suitable distance beyond the perimeter of a bone plate. Accordingly, the extension member may be configured as a tab that extends beyond the bone plate perimeter by a distance that is less than the width of the bone plate, or as an arm that extends by a distance that is greater than the width of the bone plate. The extension member may be wider than, about equal in width, or narrower than its corresponding bone plate. The extension member may have a thickness that is greater than, about the same as, or less than that of the corresponding bone plate. In some examples, an extension member that is relatively thinner than its corresponding bone plate may provide a reduced profile on bone relative to relatively thicker extension members.

The extension member may have any suitable disposition relative to a corresponding bone plate and to bone. The extension member thus may extend generally transverse of and/or in parallel to the long axis of the bone plate and/or bone. Accordingly, the extension member may extend axially and/or laterally from a bone plate, and from the end(s) and/or the side edge(s) of the bone plate. In some examples, the extension member may extend from the bone plate at least about one-eight or one-fourth of the circumference of the bone. In some examples, the extension member may extend at least to a surface region on the bone that is nonparallel and/or at least substantially perpendicular to a footprint defined on the bone by the bone plate. Accordingly, the extension member may extend substantially parallel to a plane defined by the bone plate, in a region adjacent the bone plate, and may extend substantially transverse to the plane, in a region spaced from the bone plate. The extension member may overlap the bone plate, for example, abutting the inner (bone-facing) surface and/or outer (bone-opposing) surface of the bone plate. Alternatively, the extension member may be nonoverlapping with the inner/outer surfaces of the bone plate, for example, disposed adjacent and/or in abutment with an edge of the bone plate. The extension member may connect to a bone plate near an end of the extension member, so that the extension member extends away from the bone plate from one edge of the bone plate. Alternatively, the extension member may connect to a bone plate nearer the middle of the extension member, so that the extension member extends beyond the bone plate from opposing edges of the bone plate.

The extension member may have any suitable composition. Suitable compositions may include any of the biocompatible materials (e.g., metal) described above for bone plates. The composition of the extension member may be similar or identical to that of its corresponding bone plate, or may be different (e.g., a stainless steel (or titanium alloy) extension member secured to a bone plate formed of a titanium alloy (or stainless steel)).

The extension member may have any suitable connection to a bone plate. The extension member thus may be formed integrally with the bone plate, or may be a discrete component configured to be connected to the bone plate after its formation. The extension member thus may be an optional addition to a fixation device, which may be included in or omitted from the device, as appropriate. The extension member may include one or more connective features, such as openings, projections, brackets, etc. configured to permit connection to a corresponding bone plate. For example, the extension member may include an opening(s) that can be aligned with a corresponding opening(s)/projection(s) of a bone plate. In some embodiments, the extension member may include an opening configured to be aligned with an opening or projection of the bone plate, and one or more projections configured to be received in openings of the bone plate. In some examples, the extension member may be configured to be secured to a bone plate using one or more openings of the bone plate that also or alternatively may receive fasteners to secure the bone plate to bone (e.g., if the extension member is not used for fixation).

The extension member may have any suitable connective features for securing the extension member to bone (and/or for engaging the bone) at a bone surface position spaced from the footprint of the bone plate on bone. A distal portion of the extension member (that is, a portion spaced from the bone plate) thus may include one or more connective features, such as openings, projections from the inner surface (such as prongs, pins, etc.), and/or the like, that permit the distal portion to be secured to and/or to engage bone. In some examples, the one or more connective features may include one or more openings of any suitable structure. Thus, the one or more openings may be locking (e.g., threaded), nonlocking (nonthreaded), circular, oval, and/or the like, generally as described above for bone plates in Section I. In some embodiments, the one or more openings may include an elongate opening with offset retention structures. Offset retention structures are described in more detail in the following patent application, which is incorporated herein by reference: U.S. patent application Ser. No. 11/071,050, filed Feb. 28, 2005.

Further aspects of extension members that may be suitable for the system of the present teachings are described in the following patent application, which is incorporated herein by reference: U.S. patent application Ser. No. 11/109,985, filed Apr. 19, 2005, now abandoned.

III. METHODS OF FIXING BONES USING BONE PLATES AND EXTENSION MEMBERS

The system of the present teachings may include methods of fixing bones by installing bone plates and corresponding extension members on the bones. The methods may include any suitable combination of the following steps, performed in any suitable order and any suitable number of times.

A bone for fixation may be selected. Any suitable bone may be selected having one, two, or more discontinuities, such as a humerus bone fractured at two or more positions to create three or more bone fragments.

A bone plate may be selected for fixation of the bone. The bone plate may have any suitable combination of the features described elsewhere in the present teachings.

For example, the bone plate may be sized and shaped for use on the particular bone and bone region that is fractured.

The bone plate may be secured to the bone, before, during, and/or after reduction. (Bone plates secured before or during reduction typically would be secured only partially until the reduction is completed.) Securing the bone plate may be performed by placing one or more fasteners, such as screws, wires, pins, etc., through openings of the bone plate and into the fractured bone. Generally, the bone plate may be secured to opposing sides of a discontinuity, such as a fracture, in the bone.

An extension member may be selected for additional fixation of the bone. The extension member may be selected from a set of extension members differing in overall size, shape, length, width, handedness, connection site on the bone plate, etc. The extension member may be further contoured pre- and/or peri-operatively (such as by bending the extension member), for example, to adjust how the extension member fits onto the bone plate, bone, and/or over soft tissue, or the extension member may be used without further contouring. In examples where the extension member is formed integrally with the bone plate, and/or supplied in a connected configuration, selection of the bone plate may also select the extension member.

The extension member may be coupled to the bone plate. This step of coupling may be performed before, during, and/or after the bone plate is secured to the bone. Coupling may connect the extension member to the bone plate in an adjustable configuration (e.g., movable pivotably and/or translationally with respect to the bone plate) and/or in a fixed configuration. Coupling may include apposing the extension member to a surface of the bone plate, such as the inner or outer surface of the bone plate. This apposition may align connective features of the bone plate and the extension member. Accordingly, this apposition also may include placing a projection(s) of the extension member into an opening(s) of the bone plate, and/or a projection(s) of the bone plate into an opening(s) of the extension member. The projections may be configured to restrict pivotal and/or translational motion of the extension member relative to the bone plate. The projections thus may fit snugly into the openings.

The step of coupling the extension member to the bone plate may include placing a fastener(s) through an opening(s) of the bone plate and/or extension member. In some examples, the fastener may have an external thread that engages an internal thread of an opening of the bone plate and/or of the extension member. Alternatively, or in addition, the fastener may be received in underlying bone, such as when the fastener extends through aligned openings of the bone plate and the extension member and threads into bone. The head of the fastener may engage the bone plate and/or the extension member, based, for example, on the relative disposition of these components and the direction in which the fastener is placed through the openings.

The extension member may be connected to bone at a surface position of the bone that is spaced from the bone plate. Connection of the extension member at this spaced position may include placing prongs or other projections of the extension member into bone. Alternatively, or in addition, the connection of the extension member to bone may include securing a spaced portion of the extension member to bone by placement of a fastener(s) through an opening(s) of the extension member and into the bone.

The steps described above may be used to fix multiply fractured bones. For example, the bone plate may fix a bone relative to a first fracture of a bone, and the extension member may fix the bone relative to a second fracture of the bone.

IV. KITS

The system of the present teachings may provide kits for fixing bones. The kits may include one or more bone plates, one or more extension members for coupling to the bone plates, fasteners (such as bone screws, wires, or the like) for securing the bone plate(s) and/or extension member(s) to bone and/or each other, a measurement device, a guide device, a positioning jig, a drill(s), one or more clamps, instructions for use, and/or the like. Some or all of the components of each kit may be provided in a sterile condition, such as packaged in a sterile container, and/or may be sterilizable (e.g., autoclavable).

In some examples, the kits may include a set of two or more extension members. The extension members may differ in contour, size (such as overall length and/or length of their extension regions, width, thickness, etc.), handedness (such as plate members for use on left and right bone plates), site of plate attachment, composition, target bone, distance extended along/around bone, and/or the like.

V. EXAMPLES

The following examples describe selected aspects and embodiments of the present teachings, including methods and apparatus for expanded bone fixation. These examples and the various features and aspects thereof are included for illustration and are not intended to define or limit the entire scope of the present teachings.

Example 1

An Exemplary Fixation Device for the Proximal Humerus

This example describes an exemplary fixation device, including a bone plate and an optional extension plate, for use on a proximal region of the humerus; see FIGS. 1-7. Selected aspects of FIG. 1 are described above in an overview of the present teachings.

FIGS. 1-3 show various views of left humerus 12 fractured in a proximal portion of the bone and fixed with a fixation device 14 for disposition on the exterior surface of the bone. The fixation device may include bone plate 20 and extension plate (or extension member) 22, which is affixable or affixed to the bone plate.

The bone plate may be shaped to fit on a lateral surface of the humerus. The bone plate may include a head portion 42 disposed proximally and adjacent to a body portion 44 disposed distally on the humerus (see FIG. 1). The head portion and body portion may include any suitable openings, which may be locking (e.g., threaded) or nonlocking (nonthreaded).

The head portion may be disposed toward a proximal end of the humerus, adjacent a metaphyseal (end) region of the bone. The head portion may define a plurality of locking (e.g., threaded) openings 46, elongate openings 48, and holes 50.

Locking openings 46 may be threadably engaged with threaded fasteners, such as bone screws, or may receive fasteners without threaded engagement. The elongate openings and holes may receive any suitable fasteners, such as screws, pins, and/or wires, among others.

The body portion may be disposed longitudinally on the humerus, generally parallel to the long axis the humerus and adjacent a diaphyseal (shaft) region of the bone. The body portion may define one or more elongate openings 52, circular openings (locking or nonlocking) 54, and/or smaller holes (such as for wires). The openings may include (or lack) counterbores 56 to, for example, reduce protrusion of fastener heads above the outer surface of the bone plate and/or facilitate or provide axial compression (or distraction).

The extension plate may be configured to be mounted on the bone plate and secured to the humerus. The extension plate may include an overlapping region 60 that abuts the bone plate (for example, engages the outer surface 62 (or inner surface 64) of the bone plate) and an extension region 66 that extends to a surface region of bone disposed outside the footprint of the bone plate on bone. For example, the extension region may extend partway around the humerus, to a position adjacent an anterior surface 68 of the humerus (see FIGS. 2 and 3 also). The overlapping region and/or the extension region may include one or more apertures and/or projections. In particular, the overlapping region may define a coupling aperture 70 (and, optionally, a projection extending boneward from the inner surface of the overlapping region). Furthermore, the extension region may define a spaced aperture 72 for receiving a fastener, such as a bone screw, shown at 74, and/or a hole 76 for receiving a wire (see FIG. 2). In some examples, hole 76 may be used to couple a humerus fragment provisionally to the extension plate, before a bone screw is placed through spaced aperture 72 and into the fragment.

Left humerus 12 may be multiply fractured (or cut). For example, humerus 12 may include a transverse fracture 16 spanned and stabilized by the bone plate. The bone plate may be secured to the humerus on opposing sides of the transverse fracture using bone screws, or other suitable fasteners, received in openings of the body and head portions of the bone plate and extending into bone. In particular, the bone screws may be received, for example, in elongate openings 52 of the plate's body portion (and/or head portion). The elongate openings may extend, for example, axially on the bone plate. Furthermore, the bone screws also may be received in locking openings 46 defined by the head portion. Humerus 12 also may include at least one additional fracture, such as a generally longitudinal fracture 18 extending axially and/or obliquely in the bone, generally along a path disposed between greater tuberosity 80 and lesser tuberosity 82 (see FIG. 3). The longitudinal fracture (or any other suitable discontinuity) may be spanned and fixed by the extension plate. In particular, the extension plate may be secured to the bone plate and/or bone using coupling aperture 70 and spaced aperture 72 (see FIGS. 1, 2, and 4).

FIGS. 3 and 4 show an exemplary contour of the extension plate as viewed from a position superior to the humerus (FIG. 3) or superior to a transverse section through the humerus (FIG. 4). The extension plate may include opposing end regions, for example, a proximal end region 92 that overlaps the bone plate and a distal end region 94 spaced from the bone plate and secured adjacent a surface region of the bone disposed partway around the humerus (FIG. 3). The opposing end regions may be connected by an intermediate region 96 that generally follows the surface contour of the humerus and/or that extends away from the humerus surface so that the intermediate region is spaced from the humerus surface. In some examples, the intermediate region may form a gap 98 between an inner surface 102 of the extension plate and an exterior surface region 104 of the humerus. The gap may allow, for example, soft tissue, such as a biceps tendon 106, to extend between the extension plate and bone (see FIG. 4). The overlapping region of the extension plate may generally follow the exterior surface of the bone plate. In some examples, the extension plate may bend toward the bone, shown at 110 (see FIG. 3), as the extension plate extends beyond the perimeter of the bone plate. The extension plate also may bend outward, to achieve a spaced relation to bone, as the extension plate extends over bicipital groove 112 and its overlying biceps tendon (see FIG. 4). The extension plate then may bend inward to the bone, so that a spaced region (the distal end region) of the extension plate is apposed to the bone surface, for receipt of a fastener that secures the spaced region of the extension plate to bone, outside of the footprint of the bone plate on bone.

The extension plate may be secured to the bone plate by any suitable mechanism. In some examples, the extension plate may be coupled (and/or secured) to the bone plate in a predefined disposition(s), for example, based on connective features (such as openings/projections) included in the bone plate and the extension plate. In some examples, the extension plate may be coupled to the bone plate using a coupling mechanism that restricts (and/or allows) pivotal motion and/or translational motion of the extension plate relative to the bone plate. In some examples, the extension plate may include an elongate aperture that guides translational adjustment of the extension plate before the extension plate is fixed in position.

FIG. 4 shows an exemplary coupling mechanism that may be used to couple the extension plate to the bone plate. The extension plate may have a projection 120, such as a post, extending from the inner surface of the extension plate. The projection may be sized and positioned to cooperate with coupling aperture 70 of the plate extension for alignment with a pair of locking (or nonlocking) openings 46 of the bone plate. In particular, the projection may be received in one of the bone plate openings and the plate extension positioned (e.g., pivoted) so that another of the bone plate openings is aligned with coupling aperture 70 of the plate extension. A bone screw 122 may be placed through the aligned coupling aperture and opening of the plate extension and bone plate and into bone, to couple the plate extension to the bone plate.

FIG. 5 shows an alternative coupling arrangement with a slightly modified extension plate 130. A projection 132 of the extension plate may be received in one of the locking openings and a fastener 134 (such as a screw) placed through an opening 136 of the extension plate and into threaded engagement, shown at 138, with the wall of a locking opening of the bone plate. Fastener 134 may not extend into bone, as shown in the present illustration, or may be long enough to also extend into and engage bone. In some examples, the bone plate may include two or more sets of openings with the same spacing as the projection and the opening of the extension plate, so that the extension plate may be selectively placed and coupled to the bone plate in different configurations. In some examples, the extension plate may include two or more openings in the overlapping region of the extension plate, so that two or more fasteners may be used to couple the extension plate to the bone plate (and/or bone). In some examples, the extension plate may be coupled to the bone plate with a fastener placed through a single opening of the extension plate (and without the use of a projection).

FIG. 6 shows a close-up view of extension plate 22, taken generally toward a superior edge 140 of the extension plate. Selected features of the extension plate described above in relation to FIGS. 1-4 are labeled here.

Example 2

Exemplary Bone Plate for Fixation of the Proximal Humerus

This example describes an exemplary bone plate for fixation of the proximal humerus, with or without an optional extension plate coupled to the bone plate; see FIGS. 7-8.

FIG. 7 shows bone plate 20 (also see FIGS. 1-4) in threaded engagement with bone screws 150 (and not coupled to the extension plate). Bone plate 20 may be secured to the humerus, particularly a proximal portion of the left humerus, such as on a lateral surface thereof. This bone plate may have a mirror-image counterpart for the right humerus. Alternatively, this bone plate may be configured to be secured to each of the left and right sides of the body, for example, by making the bone plate more bi-laterally symmetrical.

Head portion 42 of the bone plate may include a plurality of openings. The head portion may define openings 46 for receiving threaded fasteners, such as bone screws. Each opening 46 may be nonlocking (nonthreaded) or locking (e.g., with an internal thread). A subset of the openings, such as the openings shown at 152, may be configured to be aligned with connective features of an extension plate, as described above in Example 1, rather than, or in addition to, receiving bone screws, as shown in the present illustration. The head portion also may define one or more suture openings 48 for receiving sutures. Suture openings 48 may be disposed adjacent the perimeter of the head portion (and/or the body portion) of the bone plate. The suture openings may be elongate, such as the ovals shown, and/or wider than standard suture openings. The suture openings may be configured to permit sutures (and a suture guiding structure, such as a needle) to be received with the plate secured to bone.

FIG. 8 shows bone plate 20 and bone screws 150 viewed toward the inner surface of the bone plate. Locking openings of the bone plate may have internal threads configured to direct the bone screws along parallel and/or nonparallel paths, such as divergent and/or convergent paths, as shown here. In some cases, bone screws directed along nonparallel paths may improve the holding ability of the bone screws in bone.

Example 3

Selected Embodiments

This example describes selected embodiments of the present teachings, presented as a series of indexed paragraphs.

1. A method of fixing a humerus bone having first and second discontinuities, comprising: (A) securing a bone plate to a humerus bone such that the bone plate stabilizes the humerus bone with respect to a first discontinuity of the humerus bone; and (B) coupling a plate member to the bone plate and also to the humerus bone such that the plate member stabilizes the humerus bone with respect to a second discontinuity of the humerus bone, wherein the second discontinuity is not stabilized substantially by the step of securing.

2. The method of paragraph 1, wherein the step of securing includes a step of securing the bone plate to a lateral surface of a proximal portion of the humerus bone.

3. The method of paragraph 2, the humerus bone having a greater tuberosity and a lesser tuberosity, wherein the step of securing includes a step of securing the bone plate to the humerus bone adjacent the greater tuberosity, and wherein the step of coupling include a step of coupling the plate member to the humerus bone adjacent the lesser tuberosity.

4. The method of any preceding paragraph, wherein the step of securing stabilizes the humerus bone with respect to a transverse fracture of the humerus bone, and wherein the step of coupling stabilizes the humerus bone with respect to a substantially longitudinal fracture of the humerus bone.

5. The method of any preceding paragraph, the plate member including at least first and second openings, wherein the step of coupling includes (1) a step of placing a fastener through the first opening and into an aligned aperture of the bone plate, and (2) a step of placing another fastener through the second opening in a spaced relation to the bone plate and into the humerus bone.

6. The method of any preceding paragraph, wherein the step of coupling is performed after the step of securing.

7. The method of any preceding paragraph, wherein of the step of coupling includes a step of disposing the plate member in an overlapping configuration with the bone plate to define an overlapping region that overlaps the bone plate and an extension region that extends partway around the humerus bone from the bone plate.

8. The method of any preceding paragraph, wherein the step of coupling disposes soft tissue between the plate member and the humerus bone.

9. A method of fixing a bone, comprising: (A) securing a bone plate to a bone to define a footprint of the bone plate on the bone; and (B) coupling a plate member to the bone plate such that the plate member overlaps the bone plate and also extends away from the bone plate at least to a position adjacent a surface region of the bone that is at least substantially perpendicular to the footprint.

10. The method of paragraph 9, wherein the step of coupling includes a step of placing a fastener through an opening of the plate member and through the surface region of the bone.

11. The method of paragraph 9 or 10, wherein the step of securing includes a step of securing the bone plate to a humerus bone.

12. The method of paragraph 11, wherein the step of securing includes a step of securing the bone plate to a lateral surface of a proximal portion of the humerus bone.

13. The method of paragraph 12, wherein the step of securing include a step of coupling the plate member to the humerus bone adjacent an anterior surface of the humerus bone.

14. A method of fixing a bone, comprising: (A) securing a bone plate to a bone to define a footprint of the bone plate on the bone; and (B) coupling a plate member to the bone plate such that the plate member overlaps the bone plate and also extends away from the bone plate and over soft tissue to a position adjacent a surface region of the bone that is disposed outside the footprint.

15. The method of paragraph 14, wherein the step of coupling includes a step of placing a fastener through an opening of the plate member and through the surface region of the bone.

16. The method of paragraph 14 or 15, wherein the step of securing includes a step of securing the bone plate to a humerus bone.

17. The method of paragraph 16, wherein the step of securing includes a step of securing the bone plate to a lateral surface of a proximal portion of the humerus bone.

18. The method of paragraph 17, wherein the step of coupling includes a step of coupling the plate member to the humerus bone adjacent an anterior surface of the humerus bone.

19. The method of any of paragraphs 14-18, wherein the step of coupling disposes the plate member along a path extending partway around the bone.

20. A kit for fixing a bone, comprising: (A) a bone plate shaped to fit onto a proximal portion of a humerus bone; and (B) a plate member corresponding to the bone plate and configured to be affixed to the bone plate and also to the humerus bone in a spaced relation to the bone plate.

21. The kit of paragraph 20, the bone plate being a first bone plate, further comprising at least a second bone plate.

22. The kit of paragraph 21, wherein the first and second bone plates differ in at least one of size, shape, and composition.

23. The kit of any of paragraphs 20-22, the plate member being a first plate member, further comprising at least a second plate member.

24. The kit of paragraph 23, wherein the first and second plate members differ in at least one of size, shape, and composition.

25. The kit of any of paragraphs 20-24, further comprising at least one fastener capable of affixing the bone plate and/or plate member to bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of bone fixation, comprising:
   providing a bone plate and an extension plate, the extension plate including opposing first and second end regions and an intermediate region disposed between the first and second end regions, each of the first and second end regions and the intermediate region having a plate structure;
   securing the bone plate to a proximal portion of a humerus and overlapping the greater tuberosity of the humerus using fasteners received in openings defined by the bone plate; and
   attaching the extension plate to the bone plate and the humerus using (a) a fastener disposed in an aperture defined by the first end region and in threaded engagement with the bone plate and (b) a fastener received in an aperture defined by the second end region and extending into the humerus,
   wherein the attached extension plate extends from a position over the greater tuberosity to a position over the lesser tuberosity of the humerus such that the intermediate region is disposed over a biceps tendon.

2. The method of claim 1, wherein the step of providing a bone plate provides a bone plate including a head portion connected to a body portion, wherein the width of the head portion is greater than the width of the body portion, and wherein the extension plate overlaps the head portion of the bone plate after the step of attaching the extension plate.

3. The method of claim 2, wherein the step of securing a bone plate includes a step of securing the head portion of the bone plate to the humerus and overlapping the greater tuberosity.

4. The method of claim 1, wherein the extension plate includes an inner surface and at least one integral projection extending from the inner surface, further comprising a step of disposing the integral projection in an opening of the bone plate.

5. The method of claim 1, wherein the bone plate includes opposing inner and outer surfaces, wherein the inner surface faces the humerus after the step of securing the bone plate, and wherein the extension plate abuts the outer surface of the bone plate after the step of attaching the extension plate.

6. The method of claim 1, wherein a portion of the bone plate is disposed between the extension plate and the humerus after the step of attaching the extension plate.

7. The method of claim 1, wherein the bone plate defines a long axis, and wherein the extension plate extends transversely to the long axis after the step of attaching the extension plate, at least near a point of contact or closest approach between the bone plate and the extension plate.

8. The method of claim 1, wherein the step of attaching the extension plate is performed after the step of securing the bone plate.

9. The method of claim 1, wherein the extension plate includes an overlapping region that overlaps the bone plate and an extension region that extends away from the bone plate, and wherein the extension region is longer than the overlapping region after the step of attaching the extension plate.

10. The method of claim 1, wherein the aperture defined by the second end region of the extension plate is a locking aperture, and wherein the step of attaching the extension plate includes a step of disposing a fastener in threaded engagement with the locking aperture.

11. The method of claim 1, wherein the step of attaching the extension plate includes a step of placing a fastener through the aperture defined by the second end region and into the lesser tuberosity.

* * * * *